(12) United States Patent
Cates, Jr. et al.

(10) Patent No.: US 6,551,559 B1
(45) Date of Patent: Apr. 22, 2003

(54) SOL-GEL COATED POLARIZATION VESSELS

(75) Inventors: Gordon D. Cates, Jr., Skillman, NJ (US); Ilhan A. Aksay, Princeton, NJ (US); William Happer, Princeton, NJ (US); Ming Feng Hsu, North Haven, CT (US); Daniel Martin Dabbs, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 0 days.

(21) Appl. No.: 09/485,476

(22) PCT Filed: Aug. 13, 1998

(86) PCT No.: PCT/US98/16834

§ 371 (c)(1),
(2), (4) Date: Feb. 11, 2000

(87) PCT Pub. No.: WO99/08941

PCT Pub. Date: Feb. 25, 1999

Related U.S. Application Data

(60) Provisional application No. 60/055,290, filed on Aug. 13, 1997.

(51) Int. Cl.$^7$ .................................................. B01L 3/00
(52) U.S. Cl. .................. 422/102; 215/12.2; 427/376.2; 427/397.7; 428/34.6
(58) Field of Search ........................ 422/102; 215/12.2; 427/376.2, 397.7; 428/34.6

(56) References Cited

U.S. PATENT DOCUMENTS

| | | | |
|---|---|---|---|
| 2,807,588 A | * 9/1957 | White et al. | |
| 4,385,086 A | 5/1983 | Nakayama et al. | 427/387 |
| 4,450,407 A | 5/1984 | Kwon et al. | 324/304 |
| 4,687,652 A | * 8/1987 | Yoldas et al. | 423/327 |
| 4,786,302 A | 11/1988 | Osafune et al. | 65/3.11 |
| 5,008,219 A | 4/1991 | Hara | 501/12 |
| 5,394,057 A | 2/1995 | Russell et al. | 313/635 |
| 5,612,103 A | 3/1997 | Driehuys et al. | 428/34.7 |
| 5,617,860 A | 4/1997 | Chupp et al. | 128/653.4 |
| 5,637,507 A | 6/1997 | Wicks et al. | 436/166 |
| 5,716,424 A | * 2/1998 | Mennig et al. | 65/60.1 |

FOREIGN PATENT DOCUMENTS

JP          5-262584    * 10/1993

OTHER PUBLICATIONS

W. A. Fitzsimmons et al, Phys. Rev. Lett. 1967, 19, 943–946.*
L. B. Glebov et al, SPIE 1991, 1513, 224–231.*
H. Middleton et al, AIP Conf. Proc. 1994, 293, 244–252.*
A. A. Ahmed et al, Glass Technology 1995, 36, 54–60.*
G. Fu et al, Journal of Non–Crystalline Solids 1989, 112, 454–457.*
S. L. Heitala et al, Mat. Res. Soc. Symp. Proc. 1990, 180, 433–437.*
T. Uwabe et al, Kenkyu Hokoku—Tokyo–Toritsu Kogyo Gijutsu Senta 1993, 22, 57–60.*
B. E. Yoldas Chimika Chronika 1994, 23, 147–156.*
R. L. Gamblin et al, Physical Review 1965, 138, A946–A960.*
X. Zeng et al, Physics Letters 1983, 96A, 191–194.*
A. T. Nicol Physical Review B 1984, 29, 2397–2403.*
A. G. Williams et al, Mat. Res. Soc. Symp. Proc. 1984, 32, 151–156.*
T. Pietrab et al; Optically Polarized $^{129}$Xe in NMR Spectroscopy, Advanced Materials XP–002098966, pp 826–838.
Fitzsimmons et al., "Nature of Surface–Induced Nuclear–Spin Relaxation of Gaseous He$^3$," Physical Review, vol. 179, No. 1, pp. 156–165 (1969).
Johnson et al., "The SLAC High–Density Gaseous Polarized $^3$He Target," Nuclear Instruments and Methods in Physics Research A, vol. 356, pp. 148–152 (1995).
Haeberli, "Storage Cell Target for Polarized Proton and Antiproton Rings," International Workshop on Polarized Ion Sources and Polarized Gas Jets, Y. Mori Editor, pp. 35–44 (1990).
Heil, "Very Long Nuclear Relaxation Times of Spin Polarized Helium 3 in Metal Coated Cells," Physics Letters A, vol. 201, pp. 337–343 (1995).
Nacher et al., "Recent Results on Hyperpolarized He– $^4$He Liquid Mixtures," Czechoslovak Journal of Physics, vol. 46, Supplement S6, pp. 3025–3032 (1996).

* cited by examiner

Primary Examiner—Arlen Soderquist
(74) Attorney, Agent, or Firm—Myers Bigel Sibley & Sajovec

(57) ABSTRACT

The present invention relates to a polarization cell which is coated with glass deposited from a sol-gel used for hyperpolarizing noble gases. The invention also includes a method for hyperpolarizing noble gases utilizing the polarization cell coated with glass deposited from a sol-gel. These polarization cells can also be incorporated into containers used for storage and transport of the hyperpolarized noble gases.

32 Claims, No Drawings

SOL-GEL COATED POLARIZATION VESSELS

This application is a National Stage application of International Application Serial No. PCT/US98/16834 filed Aug. 13, 1998 and published under Article PCT 21(2) in English. The International application claims the benefit of priority of U.S. Provisional Application No. 60/055,290, filed Aug. 13, 1997.

The invention was made with U.S. Government support. The U.S. Government has certain rights in the invention.

BACKGROUND OF THE INVENTION

The invention relates to methods and apparatus for hyperpolarizing noble gases. More particularly, the invention relates to methods for manufacturing glass apparatus useful for hyperpolarizing noble gases.

The number and variety of applications of noble gases, particularly $^3$He and $^{129}$Xe, polarized through spin-exchange optical pumping (Bhaskar et al. 1982; Happer et al. 1984) have grown rapidly over the past few years. Most recently, the enhanced NMR signals of laser-polarized $^{129}$Xe, which are about five orders of magnitude larger than those from thermally polarized $^{129}$Xe, have made possible the first high-speed biological magnetic resonance imaging (MRI) of a gas (Albert et al. 1994), opening many new avenues of research. Historically, polarized $^{129}$Xe has been used for fundamental symmetry studies (Chupp et al. 1994), nuclear spin relaxation studies of solids (Gatzke et al. 1993), high resolution nuclear magnetic resonance spectroscopy (NMR) (Raftery et al. 1991), and cross-polarization to other nuclei (Gatzke et al. 1993; Driehuys et al. 1993; Long et al. 1993). Polarized $^3$He is an important nuclear target (Anthony et al. 1993; Middleton, unpublished; Newbury et al. 1991; Newbury et al. 1992) and has also been shown to be an excellent nucleus for gas-phase MRI (Middleton et al. 1995).

All of these applications require that the highly non-equilibrium polarizations of the noble gas nuclei be long-lived, i.e., the decay of polarization to thermal equilibrium level must be slow. However, interactions of the polarized noble gas nuclei with surfaces can cause rapid relaxation, often resulting in relaxation times $T_1$ that are undesirably short. Understanding these mechanisms, and devising methods of inhibiting relaxation, is vital for continued progress in a large variety of experiments using polarized noble gases.

Bouchiat and Brossel identified relaxation of hyperpolarized rubidium on coatings of paraffin on the walls of glass resonance cells (Bouchiat et al. 1966). This relaxation was attributed to adsorption of rubidium on the coatings leading to depolarizing interactions such as dipole-dipole interaction between electron spin of the rubidium atom and the nuclear spin of the protons in the coating. This paper reports a diminution of such interactions upon substituting $(CD_2)_n$ paraffins for $(CH_2)_n$ paraffins, i.e., deuterating the paraffins. Bouchiat and Brossel, however, do not extrapolate on this work and make no inferences concerning potential interactions of other elements with paraffins or the reduction thereof. Nor does this paper indicate whether any other polymeric materials exhibit depolarizing properties.

Zeng and co-workers made substantial progress in reducing $^{129}$Xe surface relaxation by introducing the use of the silicone coating agent SurfaSil (Zeng et al. 1983). Relaxation times of order $T_1 \sim 20$ min are now routinely attained using such coatings. Nonetheless, these relaxation times are still approximately two orders of magnitude shorter than what is ultimately possible for gaseous $^{129}$Xe at standard temperatures and pressures. It has been thought that continuing inability to improve nuclear spin lifetimes is attributable to paramagnetic impurities in the coating compositions. Efforts to reduce relaxation by removing such impurities, however, have met with little success. Accordingly, it is evident that better understanding of the $^{129}$Xe surface interactions has been needed.

Driehuys et al. identified polymeric coatings which further improved the properties of containers with respect to polarized noble gases. See, for example, U.S. Pat. No. 5,612,103. The polymers were modified to limit depolarizing interaction with the container surfaces. For example, contact with protons was limited by providing substituents having non-zero spin, e.g., substituting deuterium for protons. Alternatively, permeability was controlled by suitable selection of polymeric coating materials.

As a result, there exists a need for improving the yield and efficiency of noble gas hyperpolarization processes by reducing the depolarizing interactions of the noble gas with surfaces in the hyperpolarization system.

The manufacture of sol-gel materials is well known in the art. See, for example, Brinker et al. (1990). In particular, methods for manufacturing sol-gel glasses are known. See, e.g., U.S. Pat. Nos. 5,637,507, 5,008,219, and 4,385,086, the complete disclosures of which are incorporated herein by reference. Such materials can be applied as coatings. However, none of the art of which Applicants are presently aware discloses any utility for such materials in the context of preserving noble gas polarization.

There is also a need for increasing the total amount of hyperpolarization in a noble gas by reducing or counteracting depolarizing interactions between the noble gas and its surrounding physical system.

Moreover, there is a need for improving the duration of storage of hyperpolarized noble gas by reducing depolarizing interactions of the noble gas with the storage container.

In addition, there is a need for improving the efficiency of magnetic resonance imaging methods which require the use of hyperpolarized noble gas nuclei by decreasing the amount of physical interaction of the noble gas with physical systems.

SUMMARY OF THE INVENTION

In one embodiment, the invention is a polarization cell for hyperpolarizing a noble gas, wherein the polarization cell has an interior surface coated with a glass coating deposited from a sol-gel.

The noble gas is preferably $^{129}$Xe or $^3$He. The glass coating is preferably substantially impermeable to the noble gas and/or to ions in the material from which the polarization cell is manufactured. The polarization cell is preferably made of at least one material selected from the group consisting of glasses, ceramics, composites, metals. The glass coating is preferably alkali resistant. Also, the glass coating is preferably substantially free of paramagnetic or other depolarizing impurities. An especially preferred glass coating is an aluminosilicate glass.

In another embodiment, the invention is a method for hyperpolarizing a noble gas, comprising:

spin polarizing a noble gas in a polarization cell having an interior surface coated with a glass coating deposited from a sol-gel.

In another embodiment of the invention, in an apparatus for hyperpolarizing a noble gas, comprising:

a) a source of laser energy; and b) a polarization cell;

the improvement consists of a glass coating deposited from a sol-gel onto an interior surface of the polarization cell.

In still another embodiment, the invention is a method of reducing depolarizing interaction between a hyperpolarized noble gas and a surface of a container, comprising providing on the surface of the container a glass coating deposited from a sol-gel. Preferably, the container is a polarization cell, a conduit for transferring the hyperpolarized noble gas, an accumulation reservoir for accumulating the hyperpolarized noble gas, or a storage reservoir for storing the hyperpolarized noble gas.

In yet another embodiment, the invention is an apparatus for containing a hyperpolarized noble gas, wherein the apparatus has an interior surface coated with a glass coating deposited from a sol-gel. Preferred apparatus includes, for example, a polarization cell, a conduit for transferring the hyperpolarized noble gas, an accumulation reservoir for accumulating the hyperpolarized noble gas, or a storage reservoir for storing the hyperpolarized noble gas. Also included, is a transport or storage container having an interior surface coated with a glass coating deposited from a sol-gel suitable for transport or storage of the hyperpolarized noble gas.

As a result the invention provides a method and apparatus for substantially improving the production and storage of hyperpolarized noble gases. The glass coatings substantially reduce depolarizing interactions of polarized noble gas nuclei with surfaces of containers such as polarization cells, and decrease losses to permeability of the containers as well as degradative influences associated with hyperpolarization procedures.

These and other advantages of the present invention will be appreciated from the detailed description and examples which are set forth herein. The detailed description and examples enhance the understanding of the invention, but are not intended to limit the scope of the invention.

DETAILED DESCRIPTION OF THE PREFERRED EMBODIMENTS

Methods of producing hyperpolarized noble gases by spin exchange involve the use of a "polarization vessel" in which the noble gas is mixed with a vapor of alkali-metal atoms, often rubidium, and irradiated with a laser. Typically, the polarization vessels are made of glass. There are two reasons for this. First, laser light will readily pass through glass. Second, when a hyperpolarized gas such as $^3$He or $^{129}$Xe is contained in glass vessels, it will tend to depolarize relatively slowly. Put differently, one says that the "spin-relaxation time" associated with the glass is long. Constructing vessels with long spin-relaxation times is critical to obtaining and maintaining high polarizations when producing hyperpolarized gas.

Considerable effort has gone into identifying means of coating glass vessels to improve their associated spin-relaxation times. One such effort resulted in polymeric coatings described in U.S. Pat. No. 5,612,103. Other materials such as gold coatings can also be used.

It is suspected that presence of paramagnetic sites in the form of various impurities limits the spin-relaxation times that can be achieved with various glasses. For instance, it is well known that iron exists in trace quantities in most glasses. Producing extremely pure glass, however, is non-trivial. In one embodiment, our invention involves using commercially available glass, of limited purity, as the primary substance out of which the polarization vessel is fabricated. Following the fabrication of the vessel, the "sol-gel" technique is used to deposit a very pure layer of glass on the interior of the vessel. This is accomplished by injecting a solution into the finished vessel, allowing it to sit for several hours, removing the solution, and subsequently heating the sample to several hundred degrees centigrade to condense the gel to dense form. The resulting vessel presents the polarized noble gas with a particularly pristine glass surface, which results in longer spin-relaxation times.

At present, when working with $^3$He, polarization vessels are typically made out of an aluminosilicate glass. This type of glass is quite difficult to work, and only select glass blowers are capable of fabricating acceptable vessels. Using our invention, the vessels can be made out of PYREX® or other easy-to-work glasses, and subsequently coated with a glass of desired physicochemical properties. Thus, not only does our invention improve the performance of the vessels that are already in use, it also makes it possible to make vessels much more cheaply and easily.

Methods for hyperpolarizing a noble gas are known in the art, including, for example, polarization by spin exchange with an alkali metal or by metastability exchange. Suitable methods are disclosed in U.S. Pat. Nos. 5,612,103, 5,545,396, 5,642,625, and 5,617,860, the entire disclosures of which are incorporated by reference herein. Any noble gas hyperpolarization process may be employed since the effects of the invention are believed to be independent of the method by which hyperpolarization is achieved. Such methods include, for example, spin-exchange interactions with optically pumped alkali metal vapor. (Bhaskar et al. 1982; Cates et al. 1992; Bouchiat et al. 1960; Zeng et al. 1985). The optical pumping and spin-exchange can be performed using modest applied magnetic fields of about 1 G or larger. Pumping in the NMR magnet bore at fields of several Tesla is also possible. The maximum steady state $^{129}$Xe nuclear polarization achievable depends on the time constant characterizing the spin exchange with the alkali metal and the time constant characterizing the relaxation ($T_1$) due, for example, to contact with the surfaces of the pumping cell. For instance, with $T_1 \approx 20$ min, polarizations of 20–40% are quite practicable (Cates et al. 1990), and polarizations of 90% or more should be attainable. The long $T_1$ of the gas also allows samples to be manipulated, even stored as Xe ice, (Cates et al. 1990), and transported on time scales of hours or even days, without serious loss of magnetization. Even so, the invention now enables further improvement of these polarizations.

As described, the method of the invention can be used to coat the interior surfaces of polarization cells. However, any container adapted for use in handling of hyperpolarized noble gases can benefit by being coated with glass by sol-gel deposition according to the invention. For example, in apparatus in which conduits convey hyperpolarized gas from the polarization cell to another container, the conduits can be coated to reduce depolarization in transfer. Also, in hyperpolarized gas accumulation apparatus (e.g., the apparatus disclosed in U.S. application Ser. No. 08/622,865, the complete disclosure of which is incorporated by reference herein) the reservoir used for accumulation may be coated with the glass. In addition, transport or storage chambers or containers can be coated as desired which are suitable for transport or storage of the hyperpolarized noble gas.

The sol-gel composition can be deposited on an interior surface of a container otherwise adapted to contain a hyperpolarized noble gas. The deposition can be accomplished by any means known in the art for effectively coating the surface with a fluid material, such as, for example, injection, filling, dipping, spin-coating, etc. Because the contact between the noble gas and the finished container surface will be essentially continuous over the entire surface, it is preferred that at least a substantial portion of the surface be coated with the sol-gel. More preferably, the entirety of the container surface is coated with the sol-gel. The coated container may be left to age for several hours or more.

Once the contacting of the sol-gel with the container is substantially completed, any excess fluid can be evacuated from the container. A period of low temperature heating can then be imposed on the coated container to provide added mechanical robustness to the resulting coating. Then the curing of the sol-gel to the essentially "solid," densified glass phase can be commenced. Curing can be effected by heating the container interior to a temperature sufficient to cause the sol-gel to convert to a densified glass. Typically, curing requires heating the sol-gel material to a temperature of several hundred degrees centigrade (°C.). The actual temperature required for curing will depend on the glass material being deposited as the coating, and the degree of densification to be achieved, with lower temperatures yielding less densified materials.

The method of the invention finds particular use in coating glass containers which would otherwise be less than optimal in preserving the polarization of the hyperpolarized noble gas. For example, the method can be used to substantially improve the properties of glasses that would otherwise be too porous or permeable to the gas, a problem that has plagued applications involving polarized $^3$He. Alternatively, the quality of the structural glass may be such that substantial paramagnetic impurities (e.g., iron) may be present in the glass, which can induce depolarization of the noble gas. The method of the invention provides a pristine coating of high purity glass to effectively "seal" such impurities away from the polarized noble gas, limiting leaching of the impurities or diffusion of the gas into the container wall, and thereby further reducing depolarizing influences.

Thus, the method can be used to provide a coating of one type of glass onto the interior surface of a container made of a different type of glass. This is useful in those cases in which the structure of the vessel is difficult to manufacture using certain types of glass but which is easier using cheaper or poorer quality glass. The sol-gel coating can the be applied to the pre-formed vessel structure to provide the desired properties. It is known, for example, that blowing of aluminosilicate glass is difficult, requiring special expertise. The method of the invention permits vessel manufacture by blowing conventional borosilicate glass, which can be accomplished more quickly, by those of lesser skill, and with fewer defects. The cost of vessel manufacture is thereby lessened, and practice of hyperpolarization thereby rendered easier.

The method and apparatus of the invention also finds utility in those applications in which the polarization process can exert substantial degradation upon the polarization cell. For example, in those processes in which an alkali metal such as rubidium is employed to induce polarization of the noble gas by the spin exchange method, the inherent reactivity of the alkali metal can cause degradation of glasses such as PYREX®. The invention enables the deposition of a glass which is intrinsically resistant to reaction with alkali metal vapor. Such glasses as aluminosilicate materials possess this property, and are especially desirable.

The glass deposited from the sol-gel can be deposited onto any material with which it is physically or chemically compatible. The glass coating can be deposited onto substrate materials such as glasses, ceramics, silicon and silicas, composites, and metals. Adherence to the substrate material is known to depend on factors such as surface wettability and thermal expansion properties. Accordingly, it is preferred that the substrate and the glass coating have similar thermal expansion coefficients. However, some thermal coefficient mismatch is acceptable, especially when relatively thin coatings are used. This is important for purposes of ensuring structural integrity (mechanical robustness) during the curing process, but is still more important to ensure stability and integrity during the hyperpolarization process when repeated exposures to high temperatures are routine.

The sol-gel coating can be deposited in a single application with subsequent curing. Alternatively, the sol-gel coating can be deposited in several applications. For example, the container surface can be contacted with the sol-gel and allowed to dry, with these steps repeated one or more times prior to curing. Alternatively, a plurality of complete applications including at least the contacting and curing steps can be performed in series, so that a coated container can be re-coated and re-cured any desired number of times.

The thickness of the coating on the surface should be such as to substantially minimize depolarizing interaction with the surface of the container. Thus, the coating is preferably of a thickness sufficient to substantially eliminate the interactions relating to diffusion of the noble gas to the substrate. The coating should be sufficient to substantially eliminate migration of paramagnetic impurities from the substrate. Also, the coating should be sufficiently thick to impart alkali resistance to the container.

The glass coating, therefore, should be at least about 0.1 nm (1 nm=$10^{-9}$ meter), preferably at least about 10 nm, and more preferably at least about 100 nm thick. Coatings in the range of from about 0.1 $\mu$m (1 $\mu$m=$10^{-6}$ meter) to about 10 $\mu$m are preferred.

A highly preferred sol-gel for use according to the invention is a solution comprising Al(NO$_3$)$_3$.9H$_2$O and Si(OC$_2$H$_5$)$_4$ dissolved in ethanol. The components of the composition hydrolyze in the presence of water to provide hydroxides, which then react to provide an aluminosilicate glass upon curing. Other comparable and functionally equivalent sol-gel materials can be employed. For example, other metal alkoxides can be employed, as can other organic solvents. The nature of the resulting glass can be controlled by adjusting the pH of the sol-gel. Accordingly, acid catalysts can be used.

The magnitude of the increase in relaxation time made possible through the invention now permits a substantial increase in the efficiency of noble gas hyperpolarization processes, as well as an increase in the efficiency and practicability of methods which depend on the use of hyperpolarized noble gases. In addition to the practical implications for improvements in polarized noble gas technology, this invention should be of particular interest in the further development of NMR-based procedures with laser-polarized noble gases. A particularly significant procedure which can take advantage of the extended polarization lifetimes enabled by the invention is medical nuclear magnetic resonance imaging of in vitro and in vivo biological systems, such as is described in U.S. Pat. No. 5,545,396, the entire disclosure of which is incorporated herein by reference.

EXAMPLE

An exemplary sol-gel coating is described for purposes of illustrating the invention. Into 50 mL ethanol is dissolved 46.3 g Al(NO$_3$)$_3$.9H$_2$O. The mixture is stirred overnight to yield a homogeneous solution. To the solution is added 12.9 g Si(OC$_2$H$_5$)$_4$ (tetraethylortho-silicate or tetraethoxysilane) with mixing. The resulting solution yields about 10 g Al$_2$O$_3$ and SiO$_2$ in 50% molar concentration in ethanol. This solution is diluted (1 part neat solution to 15 parts ethanol) to provide a coating solution. The dilution factor can be adjusted to control solution viscosity, with concomitant control of coating thickness. Cracking is observed to occur more frequently with thicker films.

The interior of a polarization cell blown from PYREX® glass is contacted with the coating solution, by filling the cell with the solution. After two hours, the solution is evacuated from the cell by dumping out the excess. The contacted cell is then cured overnight at a slightly elevated temperature, e.g., from about ambient temperature to about 100° C., preferably about 60° C., to impart additional robustness to the coating before high temperature treatment. Then the coated cell is subjected to a high temperature heat treatment, by raising the temperature at a rate of 5° C./min to 500° C., and maintained at this temperature for two hours. Slow ramping of temperature is preferable to avoid heat shock and cracking. The cured coating is an aluminosilicate glass of high purity.

Applicants have determined that the thickness of the resulting coating is in the range of from about 0.2 $\mu$m to about 0.6 $\mu$m when heated to a temperature of 400° C. or more. Full densification of the glass appears to occur by heating to about 400° C., with higher temperatures not yielding significant additional densification. Lower temperatures can be employed if less dense coatings are desired.

The aluminosilicate glass coating resulting from the process described above is an excellent barrier to ion migration from the underlying substrate. Applicants have calculated that the concentration of ions (e.g., iron ions) migrating from a borosilicate glass substrate into the fully densified coating will drop by a magnitude of 5 over a distance of about $10^{-4}$ $\mu$m. Accordingly, ion diffusion is substantially eliminated. If the glass is not fully densified, it would be expected that ion migration would be greater.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

BIBLIOGRAPHY

The following publications, mentioned in the foregoing specification, are incorporated herein by reference for all that they disclose:

Albert M S, Cates G D, Driehuys B, Happer W, Saam B, Springer C S, and Wishnia A, *Nature* 370:188 (1994).

Anthony P L, et al., *Phys Rev Lett* 71:959 (1993).

Bhaskar N D, Happer W, and McClelland T, *Phys Rev Lett* 49:25 (1982).

Bouchiat M A, Carver T R, and Varnum C M, *Phys Rev Lett* 5:373 (1960).

Bouchiat M A, and Brossel J, *Phys Rev,* 147:41 (1966).

Brinker J and Scherer G, *Sol-Gel Science and Technology,* Academic Press (1990).

Cates G D, Benton D R, Gatzke M, Happer W, Hasson K C, and Newbury N R, *Phys Rev Lett,* 65:2591 (1990).

Cates G D, Fitzgerald R J, Barton A S, Bogorad P, Gatzke M, Newbury N R and Saam B, *Phys Rev A* 45:4631 (1992).

Chupp T E, Hoare R J, Walsworth R L, and Wu B, *Phys Rev Lett* 72:2363 (1994).

Driehuys B, Cates G D, Happer W, Mabuchi H, Saam B, Albert M S, and Wishnia A, *Phys Lett A* 184:88 (1993).

Gatzke M, Cates G D, Driehuys B, Fox D, Happer W, and Saam B, *Phys Rev Lett* 70:690 (1993).

Happer W, Miron E, Schaefer S, van Wijngaarden, and Zeng X, *Phys Rev A* 29:3092 (1984).

Long H W, Gaede H C, Shore J, Reven L, Bowers C R, Kritzenberger J, Pietrass T, Pines A, Tang P, and Reimer J A, *J Am Chem Soc* 115:8491 (1993).

Middleton H, PhD Thesis, Princeton University, unpublished.

Middleton H, et al., *Magnetic Resonance in Medicine* 33:271 (1995).

Newbury N R, et al., *Phys Rev Lett* 67:3219 (1991).

Newbury N R, et al., *Phys Rev Lett* 69:391 (1992).

Raftery D, Long H, Meersmann T, Grandinetti P J, Reven L, and Pines A, *Phys Rev Lett* 66:584 (1991).

Zeng X, Miron E, van Wijngaarden W A, Schreiber D, and Happer W, *Phys Lett* 96A:191 (1983).

Zeng X, Wu Z, Call T, Miron E, Schreiber D, and Happer W, *Phys Rev A* 31:260 (1985).

What is claimed is:

1. A polarization cell for hyperpolarizing a noble gas comprising a vessel having a space therein holding a quantity of noble gas and alkali metal having a vapor phase therein, wherein said polarization vessel comprises an interior surface coated with a glass coating deposited from a sol-gel and is configured to allow laser energy to enter therein to thereby optically pump the alkali metal vapor, wherein the sol-gel coating is configured to withstand exposures to spin-exchange interactions with the optically pumped alkali metal vapor during hyperpolarization of the noble gas in the polarization vessel, and wherein, during operation, the polarization vessel first holds the noble gas in a non-hyperpolarized state and then, after hyperpolarization, holds the noble gas in a hyperpolarized state.

2. A polarization cell for hyperpolarizing a noble gas according to claim 1, further comprising a quantity of one or more of $^{129}$Xe and $^3$He held therein, wherein the substrate has a first thermal expansion coefficient and the sol-gel coating has a second thermal expansion coefficient, and wherein the first and second thermal expansion coefficients are similar so as to promote the integrity of the coating during exposures to elevated temperatures during operation of the polarization cell to thereby inhibit the formation of cracks.

3. A polarization cell according to claim 1, wherein the glass coating is substantially free of depolarizing impurities.

4. A polarization cell according to claim 1, wherein the glass coating is an aluminosilicate glass.

5. A polarization cell according to claim 1, wherein the vessel is made of at least one material selected from the group consisting of glasses, ceramics, composites, and metals.

6. A polarization cell according to claim 1, further comprising a quantity of polarized $^{129}$Xe held therein, wherein the polarization vessel comprises a glass substrate material that defines the uncoated interior surface thereof, and wherein the sol gel coating is an aluminosilicate coating.

7. A polarization cell according to claim 1, further comprising a quantity of polarized $^3$He held therein, wherein the polarization vessel comprises a glass substrate material that defines the uncoated interior surface thereof, and wherein the sol gel coating is an aluminosilicate coating.

8. A polarization cell according to claim 1, wherein the vessel comprises a borosilicate glass substrate material that defines the uncoated interior surface thereof, and wherein the sol-gel coating is an aluminosilicate coating.

9. A method for hyperpolarizing a noble gas, comprising:
   spin polarizing a noble gas in a polarization cell having an interior surface coated with a glass coating deposited from a sol-gel.

10. In an apparatus for hyperpolarizing a noble gas, comprising:
   a) a source of laser energy;
   b) a polarization cell;
the improvement consisting of a glass coating deposited from a sol-gel onto an interior surface of said polarization cell.

11. A method of reducing depolarizing interaction between a hyperpolarized noble gas and a surface of a container, comprising;
   providing on the surface of the container a glass coating deposited from a sol-gel in sufficient thickness and formulation so that the coated surface is substantially impermeable to the noble gas and/or to ions in the underlying container material to thereby inhibit depolarizing interaction between the hyperpolarized noble gas and the container, wherein the substrate and coating each have a thermal expansion coefficient that is similar to the other, and wherein the coated container yields an extended polarization relaxation time ($T_1$) relative to that of a corresponding uncoated container.

12. A method according to claim 11, wherein the container is a polarization cell, a conduit for transferring the hyperpolarized noble gas, an accumulation reservoir for accumulating the hyperpolarized noble gas or a storage reservoir for storing the hyperpolarized noble gas.

13. An apparatus having interior hyperpolarized noble gas contacting surfaces, wherein at least a portion of said interior hyperpolarized noble gas contacting surfaces is coated with a glass coating deposited from a sol-gel, and wherein the coating is a high purity aluminosilicate coating formulated so as to be substantially impermeable to the noble gas and/or to ions in the underlying material of the hyperpolarized gas contacting surfaces.

14. An apparatus according to claim 13, further comprising a quantity of hyperpolarized noble gas.

15. An apparatus according to claim 14, wherein said apparatus is a transport or storage container configured to hold said hyperpolarized noble gas therein.

16. An apparatus according to claim 15, wherein said hyperpolarized noble gas is hyperpolarized $^{129}$Xe or $^3$He.

17. An apparatus according to claim 14, wherein the hyperpolarized gas comprises $^{129}$Xe, and wherein the sol gel coating is an aluminosilicate coating.

18. An apparatus according to claim 14, wherein the hyperpolarized gas comprises $^3$He, and wherein the sol gel coating is an aluminosilicate coating.

19. An apparatus according to claim 13, wherein the gas contacting surface is formed over an underlying substrate, and wherein the substrate has a first thermal expansion coefficient and the sol-gel coating has a second thermal expansion coefficient, and wherein the first and second thermal expansion coefficients are similar.

20. A method of fabricating a polarization cell configured to polarize a quantity of noble gas during polarization of the gas, comprising the steps of:

inserting a quantity of fluid sol-gel into a polarization cell comprising a space with internal hyperpolarized noble gas contacting surfaces and at least one port for receiving a quantity of hyperpolarized noble gas therein; and depositing a quantity of the inserted sol-get onto a substantial portion of the gas contacting surfaces, wherein, the sol-gel coated polarization cell has an associated extended polarization relaxation time ($T_1$) compared to a corresponding non sol-gel coated polarization cell.

21. A method according to claim 20, wherein said method further comprises the step of heating said inserted so-gel to a curing temperature.

22. A method according to claim 21, wherein said polarization cell is formed of a glass body.

23. A method according to claim 21, wherein after said curing step, the polarization cell is configured to allow laser emitted rays to pass through a portion of said coated gas contacting surfaces.

24. A method according to claim 23, further comprising introducing a quantity of noble gas and alkali metal into the sol-gel coated polarization cell; and polarizing the noble gas via spin exchange between a quantity of the noble gas and the alkali metal excited by the emitted laser rays, wherein said sol gel is an aluminosilicate.

25. A method according to claim 24, wherein the coated polarization cell is configured to inhibit alkali metal induced degradation of the integrity of the coating.

26. A method according to claim 24, wherein the noble gas comprises $^{129}$Xe.

27. A method according to claim 24, wherein the noble gas comprises $^3$He.

28. A method according to claim 21, wherein said after said curing step said polarization cell is configured to inhibit the surface-relaxation attributed to contact of the hyperpolarized gas therewith.

29. A method according to claim 20, further comprising introducing at least one of $^{129}$Xe and $^3$He gas into the sol-gel coated polarization cell; and then polarizing the gas in the sol-gel coated polarization cell.

30. A method according to claim 20, wherein the gas contacting surfaces have a corresponding thermal expansion coefficient and the sol-gel coating is formulated to have a thermal expansion coefficient that is similar thereto.

31. A polarization cell for hyperpolarizing a noble gas having a space with a quantity of noble gas and alkali metal having a vapor phase held therein, wherein said polarization cell comprises a glass substrate material with an interior surface coated with a high purity aluminosilicate coating deposited from a sol-gel, the substrate and coating each having a thermal expansion coefficient that is similar to the other, said substrate and coating being configured to allow laser energy to enter therein to thereby optically pump the alkali metal vapor, wherein the sol-gel deposited coating on the substrate is configured to withstand exposure to spin-exchange interactions with the optically pumped alkali metal vapor during hyperpolarization of the noble gas and to inhibit depolarizing interaction between the hyperpolarized noble gas and the polarization cell.

32. A polarization cell for hyperpolarizing a noble gas, said cell comprising a quantity of noble gas and alkali metal having a vapor phase held therein, wherein said polarization cell comprises a glass substrate material with an interior surface coated with a glass coating deposited from a sol-gel, the substrate and sol-gel coating each having a thermal expansion coefficient that is similar to the other, the sol-gel being selected so that it is substantially impermeable to the noble gas and/or to ions in the glass substrate material, said substrate and coating being configured to allow laser energy to enter therein to thereby optically pump the alkali metal vapor, wherein the sol-gel deposited coating on the substrate is configured to withstand exposure to spin-exchange interactions with the optically pumped alkali metal vapor during hyperpolarization of the noble gas.

* * * * *